(12) United States Patent
Teng et al.

(10) Patent No.: US 6,635,649 B2
(45) Date of Patent: Oct. 21, 2003

(54) PIPERAZINEDIONE COMPOUNDS

(76) Inventors: Che-Ming Teng, 100 Sgy-Wei Road, Taipei 106 (TW); Hui-Po Wang, 3rd Fl., 13, Lane 199 Shin-Yi Road., Sec. 4, Taipei 106 (TW); Eric I. C. Li, No. 74-1 Lane 93 Tung-Lin Road, Tainan City (TW); On Lee, No. 74-1 Lane 93 Tung-Lin Road, Tainan City (TW); Jih-Hwa Guh, B1 Fl., No. 60, Lane 394 Wu-Shin Street, Taipei 110 (TW); Huei-Ting Chen, 4th Fl., 27, Lane 143 Ren-Ai Road, Sec. 3, Taipei (TW); Ya-Bing Fan, 35, Fwu-Tay Street Tay-Shan 243, Taipei (TW); Ya-Lan Chen, No. 26-1, Lane 112 Wei-Kuo Street, East Area, Tainan City (TW)

( * ) Notice: Subject to any disclaimer, the term of this patent is extended or adjusted under 35 U.S.C. 154(b) by 0 days.

(21) Appl. No.: 09/851,077

(22) Filed: May 8, 2001

(65) Prior Publication Data

US 2002/0028819 A1 Mar. 7, 2002

Related U.S. Application Data

(60) Provisional application No. 60/304,191, filed on May 9, 2000, now abandoned.

(51) Int. Cl.[7] ............... A61K 31/496; A61K 31/497; C07D 401/06; C07D 409/14
(52) U.S. Cl. ............... 514/253.11; 514/252.11; 514/253.12; 544/360; 544/364
(58) Field of Search ............... 544/360, 364, 544/405; 514/253.11, 253.12, 252.11

(56) References Cited

U.S. PATENT DOCUMENTS

| | | | | |
|---|---|---|---|---|
| 4,940,709 A | * | 7/1990 | Shimazaki et al. | 514/253 |
| 5,700,804 A | | 12/1997 | Collins et al. | 514/255 |
| 5,902,812 A | | 5/1999 | Brocchini et al. | 514/253 |

FOREIGN PATENT DOCUMENTS

| WO | 95/21832 | * | 8/1995 |
|---|---|---|---|

OTHER PUBLICATIONS

Kondoh et al., Journal of Antibiotics, vol. 51, p. 801–804 (1998).*

Kunishima et al., J.Am. Chem. Soc. vol. 121, p. 4722–4723 (May,1999).*

Hayashi, et al. *Total Synthesis of Anti–microtubules Diketopiperzine Derivatives: Phenyahistin and Aurantiamine*. J. Org. Chem. Dec. 1, 2000;65(24):8402–5.

Kanoh, et al. *Synthesis and Biological Activities of Phenylahistin Derivatives*. Bioorg. Med. Chem. Jul. 1999; 7(7): 1451–7.

Kanoh, et al. *Antitumor Activity of Phenylahistin In Vitro and In Vivo*. Biosci. Biotechnol. Biochem. Jun. 1999; 63(6):130–3.

Kanoh, et al. *(–)–Phenylahistin Arrests Cells In Mitosis By Inhibiting Tubulin Polymerization.*. J. Antibiot (Tokyo). Feb. 1999;52(2):134–41.

* cited by examiner

*Primary Examiner*—Emily Bernhardt

(57) ABSTRACT

Piperazinedione compounds of the formula:

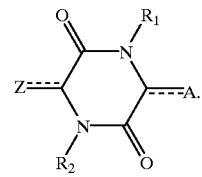

Each of and ==== and ---- independently, is a single bond or a double bond; A is H or $CH(R^a R^b)$ when ==== is a single bond, or $C(R^a R^b)$ when is a double bond; Z is $R_3O$—(Ar)—B, in which B is $CH(R^c)$ when ==== is a single bond, or $C(R^c)$ when ==== is a double bond; Ar is heteroaryl; and $R_3$ is H, alkyl, aryl, heteroaryl, $C(O)R^d$, $C(O)OR^d$, $C(O)NR^d R^e$, or $SO_2R^d$; each of $R^1$ and $R^2$, independently, is H, $C(O)R^d$, $C(O)OR^d$, $C(O)NR^d R^e$, or $SO_2R^d$; and each of $R^a$, $R^b$, $R^c$, $R^d$, and $R^e$, independently, is H, alkyl, aryl, heteroaryl, cyclyl, or heterocyclyl. Optionally, $R^a$ and $R^b$ taken together are cyclyl or heterocyclyl; and, also optionally, $R_1$ and $R^a$ or $R_1$ and $R^b$ taken together are cyclyl or heterocyclyl. Also disclosed is a method for treating tumor with the above described piperazinedione compounds.

23 Claims, No Drawings

PIPERAZINEDIONE COMPOUNDS

RELATED APPLICATION

This application claims priority from U.S. provisional application No. 60/304,191, filed on May 9, 2000, now abandoned, the contents of which are incorporated herein by reference.

BACKGROUND

The treatment of tumor can be approached by several modes of therapy, including surgery, radiation, chemotherapy, or any combination of any of these treatments. Among them, chemotherapy is indispensable for inoperable or metastatic forms of cancer. Considering the diversity of tumors in terms of cell type, morphology, growth rate, and other cellular characteristics, the U.S. National Cancer Institute (NCI) has developed a "disease-oriented" approach to anti-tumor activity screening. Boyd, M. R. (1989) In *Principle of Practice of Oncology Devita*, J. T., Hellman, S., and Rosenberg, S. A. (Eds.) Vol. 3, PPO Update, No. 10. This in vitro screening system is based on human tumor cell line panels consisting of approximately 60 cell lines of major human tumors (e.g., leukemia, lung cancer, colon cancer, CNS cancer, melanoma, ovarian cancer, renal cancer, prostate cancer, or breast cancer), and serves as a tool for identifying compounds that possess anti-tumor activities.

Of particular interest are the anti-tumor compounds that function via one or more of the following four mechanisms: (1) inhibiting $G_2/M$ progression of the cell cycle, which might eventually induce the apoptosis in tumor cells (Yeung et al. (1999) *Biochem. Biophys. Res. Com.* 263: 398–404); (2) disturbing tubulin assembly/dissembly, which may inhibit the cell mitosis and induce the cell apoptosis (Panda et al. (1997) *Proc. Natl. Acad. Sci. USA* 94:10560–10564); (3) inhibiting endothelial cell proliferation and angiogenesis effect (Witte et al. (1998) *Cancer Metastasis Rev.* 17: 155–161; Prewett et al. (1999) *Cancer Res.* 59:5209–5218); or (4) regulating Ras protein-dependent signal transduction pathway (Hernandez-Alcoceba et al. (2000) *Cell Mol. Life Sci.* 57: 65–76; Buolamwini (1999) *Cur. Opin. Che. Biol.* 3: 500–509).

SUMMARY

This invention is based in part on the discovery that piperazinedione compounds have anti-tumor activities, identified by NCI screening system, and function via one or more of the above-mentioned four mechanisms.

An aspect of the present invention relates to piperazinedione compounds of formula:

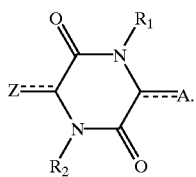

Each of ==== and ==== independently, is a single bond or a double bond; A is H or $CH(R^aR^b)$ when ==== is a single bond, or $C(R^aR^b)$ when ==== is a double bond. Z is $R_3O$—(Ar)—B, in which B is $CH(R^c)$ when ==== is a single bond, or $C(R^c)$ when ==== is a double bond; Ar is heteroaryl; $R_3$ is H, alkyl, aryl, heteroaryl, $C(O)R^d$, $C(O)OR^d$, $C(O)NR^dR^e$, or $SO_2R^d$; and both B and $R_3O$ can be substituted at any suitable position on Ar. Each of $R_1$ and $R_2$, independently, is H, $C(O)R^d$, $C(O)OR^d$, $C(O)NR^dR^e$, or $SO_2R^d$; and each of $R^a$, $R^b$, $R^c$, $R^d$, and $R^e$, independently, is H, alkyl, aryl, heteroaryl, cyclyl, or heterocyclyl. Optionally, $R^a$ and $R^b$ taken together are cyclyl or heterocyclyl; and, also optionally, $R_1$ and $R^a$ or $R_1$ and $R^b$ taken together are cyclyl or heterocyclyl.

Referring to the above formula, a subset of the piperazinedione compounds of this invention is featured by that both ==== and ==== are double bonds. In these compounds, Ar is pyridyl linked to B at position 2, $R^c$ is H, $R_3O$ is arylalkoxy linked to position 5 of pyridyl, both $R_1$ and $R_2$ are H, one of $R^a$ and $R^b$ is aryl or heteroaryl, and the other of $R^a$ and $R^b$ is H. Another subset of the piperazinedione compounds of this invention is featured by that both ==== and ==== are single bonds. In these compounds, Ar is pyridyl linked to B at position 2, $R^c$ is H, $R_3O$ is arylalkoxy linked to position 5 of pyridyl, both $R_1$ and $R_2$ are H, one of $R^a$ and $R^b$ is H, aryl, or heteroaryl, and the other of $R^a$ and $R^b$ is H.

Alkyl, aryl, heteroaryl, cyclyl, and heterocyclyl mentioned herein include both substituted and unsubstituted moieties. The term "substituted" refers to one or more substituents (which may be the same or different), each replacing a hydrogen atom. Examples of substituents include, but are not limited to, halogen, hydroxyl, amino, alkylamino, arylamino, dialkylamino, diarylamino, cyano, nitro, mercapto, carbonyl, carbamido, carbamyl, carboxyl, thioureido, thiocyanato, sulfoamido, $C_1$~$C_6$ alkyl, $C_1$~$C_6$ alkenyl, $C_1$~$C_6$ alkoxy, aryl, heteroaryl, cyclyl, heterocyclyl, wherein alkyl, alkenyl, alkoxy, aryl, heteroaryl cyclyl, and heterocyclyl are optionally substituted with $C_1$~$C_6$ alkyl, aryl, heteroaryl, halogen, hydroxyl, amino, mercapto, cyano, or nitro. The term "aryl" refers to a hydrocarbon ring system having at least one aromatic ring. Examples of aryl moieties include, but are not limited to, phenyl, naphthyl, and pyrenyl. The term "heteroaryl" refers to a hydrocarbon ring system having at least one aromatic ring which contains at least one heteroatom such as O, N, or S. Examples of heteroaryl moieties include, but are not limited to, furyl, fluorenyl, pyrrolyl, thienyl, oxazolyl, imidazolyl, thiazolyl, pyridinyl, pyrimidinyl, quinazolinyl, and indolyl.

Another aspect of the present invention relates to a pharmaceutical composition that contains a pharmaceutically acceptable carrier and an effective amount of at least one of the piperazinedione compounds described above.

A further aspect of this invention relates to a method for treating tumor (e.g., leukemia, lung cancer, colon cancer, CNS cancer, melanoma, ovarian cancer, renal cancer, prostate cancer, or breast cancer). The method includes administering to a subject in need thereof an effective amount of the piperazinedione compound having the formula:

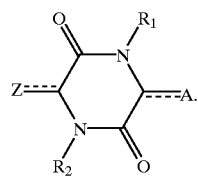

Each of ==== and ====, independently, is a single bond or a double bond; A is H or CH(R$^a$R$^b$) when ==== is a single bond, or C(R$^a$R$^b$) when ==== is a double bond, Z is CH(R$^c$R$^d$) when ==== is a single bond, or C(R$^c$R$^d$) when ==== is a double bond; each of R$_1$ $_{and\,R2}$, independently, is H, C(O)R$^e$, C(O)OR$^e$, C(O)NR$^e$R$^f$, or SO$_2$R$^e$; and each of R$^a$, R$^b$, R$^c$, R$^d$, R$^e$, and R$^f$, independently, is H, alkyl, aryl, heteroaryl, cyclyl, or heterocyclyl, provided that one of R$^c$ and R$^d$ is aryl or heteroaryl. If ==== is a double bond, ==== is a single bond, and one of R$^c$ and R$^d$ is H, then the other of R$^c$ and R$^d$ is heteroaryl. Optionaly, R$^a$ and R$^b$ taken together are cyclyl or heterocyclyl; and, also optionally, R$_1$ and R$^a$ or R$_1$ and R$^b$ taken together are cyclyl or heterocyclyl.

Referring to the above formula, a subset of the just-described piperazinedione compounds is featured by that both ==== and ==== are double bonds. In these compounds, one of R$^c$ and R$^d$ is 2-pyridyl, the other of R$^c$ and R$^d$ is H, both R$_1$ and R$_2$ are H, one of R$^a$ and R$^b$ is aryl or heteroaryl, and the other of R$^a$ and R$^b$ is H. The 2-pyridyl can be further substituted with 5-arylalkoxy. Another subset of the piperazinedione compounds is featured by that both ==== and ==== are single bonds. In these compounds, one of R$^c$ and R$^d$ is 2-pyridyl, the other of R$^c$ and R$^d$ is H, both R$_1$ and R$_2$ are H, one of R$^a$ and R$^b$ is H, aryl, or heteroaryl, and the other of R$^a$ and R$^b$ is H.

Seven exemplary piperazinedione compounds are 3-[(5-benzyloxypyridin-2-yl)methylidene]-6-phenylmethylidene piperazine-2,5-dione, 3-[(5-benzyloxypyridin-2-yl) methylidene]-6-p-hydroxyphenylmethylidenepiperazine-2, 5-dione, 3-[(5-benzyloxypyridin-2-yl)methylidene]-6-p-fluorophenylmethylidenepiperazine-2,5-dione, 3-[(5-benzyloxypyridin-2-yl)methylidene]-6-p-chlorophenylmethylidenepiperazine-2,5-dione, 3-[(5-benzyloxypyridin-2-yl)methylidene]-6-p-phenylmethoxy phenylmethylidenepiperazine-2,5-dione, 3-[(5-benzyloxypyridin-2-yl)methylidene]-6-[(thien-2-yl) methylidene]piperazine-2,5-dione, and 3,6-di [(5-benzyloxypyridin-2-yl)methyl]piperazine-2,5-dione. Their structures are shown below:

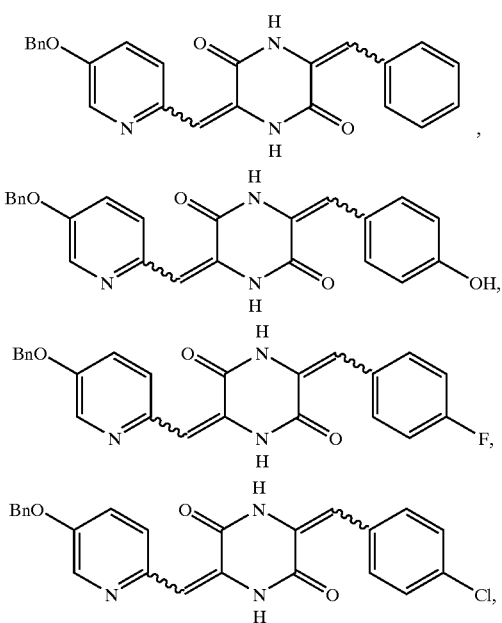

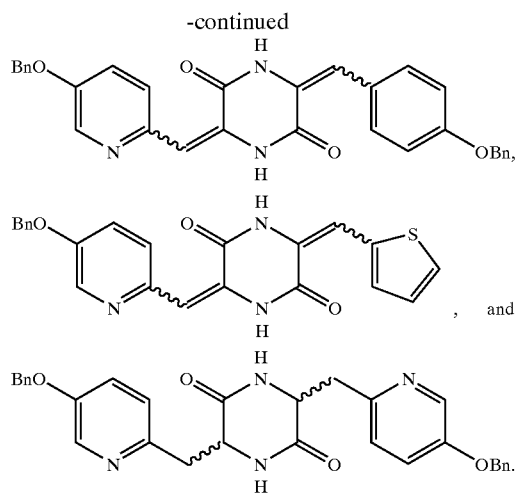

The piperazinedione compounds described above include the compounds themselves, as well as their salts and their prodrugs, if applicable. Such salts, for example, can be formed between a positively charged substituent (e.g., amino) on a piperazinedione compound and an anion. Suitable anions include, but are not limited to, chloride, bromide, iodide, sulfate, nitrate, phosphate, citrate, methanesulfonate, trifluoroacetate, and acetate. Likewise, a negatively charged substituent (e.g., carboxylate) on a piperazinedione compound can form a salt with a cation. Suitable cations include, but are not limited to, sodium ion, potassium ion, magnesium ion, calcium ion, and an ammonium cation such as teteramethylammonium ion. Examples of prodrugs include esters and other pharmaceutically acceptable derivatives, which, upon administration to a subject, are capable of providing piperazinedione compounds described above.

Also within the scope of this invention are a composition containing one or more of the piperazinedione compounds described above for use in treating tumor, and the use of such a composition for the manufacture of a medicament for the just-described use.

Other features or advantages of the present invention will be apparent from the following detailed description of several embodiments, and also from the appending claims.

DETAILED DESCRIPTION

The piperazinedione compounds described above can be prepared by methods well known in the art, as well as by the synthetic routes disclosed herein. For example, one can react a piperazine-2,5-dione compound with a heteroaryl formaldehyde to produce an intermediate heteroaryl-methylidene-piperazine-2,5-dione. The intermediate can then be reduced to heteroaryl-methyl-piperazine-2,5-dione (a compound of this invention), or reacted with a ketone or another formaldehyde, followed by a base treatment, to produce a mixture of piperazinedione isomers, which are cis- or trans- or E- or Z-double bond isomeric forms. The desired isomeric product can be separated from others by high pressure liquid chromatography (HPLC). If preferred, proper functional groups can be introduced into the heteroaryl ring by further modifications. Alternatively, a desired reduced product can be obtained by reacting the product with a reducing agent.

Shown below is a scheme that depicts the synthesis of seventeen piperazinedione compounds.

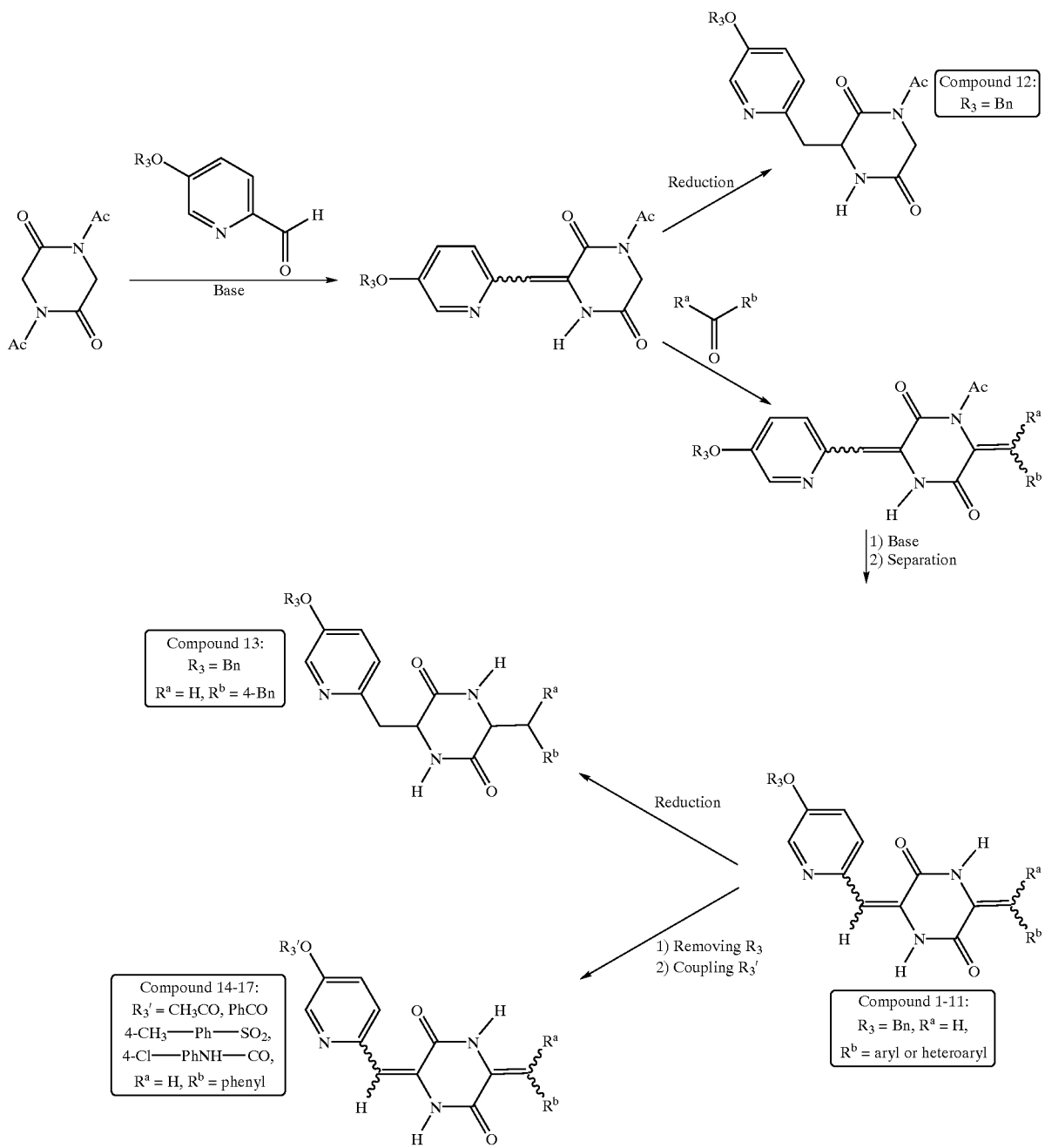

Details of synthesis of Compounds 1–17 are described in Examples 1–17, respectively. To prepare other piperazinedione compounds, the pyridinyl (shown in the above scheme) can be replaced by an aryl or another heteroaryl (e.g., furyl, pyrrolyl, imidazolyl, pyrimidinyl, or indolyl), and one of the two acetyl groups (Ac) on the piperazinedione ring (also shown in the above scheme) can be replaced by another substituent (e.g., carbonyl, carbamido, carbamyl, or carboxyl).

Note that the piperazinedione compounds contain at least two double bonds, and may further contain one or more asymmetric centers. Thus, they can occur as racemates and racemic mixtures, single enantiomers, individual diastereomers, diastereomeric mixtures, and cis- or trans- or E- or Z-double bond isomeric forms. All such isomeric forms are contemplated.

Also within the scope of this invention is a pharmaceutical composition that contains an effective amount of at least one piperazinedione compound of the present invention and a pharmaceutically acceptable carrier. Further, this invention covers a method of administering an effective amount of one or more of the piperazinedione compounds described in the "Summary" section above to a subject in need of tumor treatment. The piperazinedione compounds can function via one or more of the above described action mechanisms, or via any other mechanism. "An effective amount" refers to the amount of the compound which is required to confer a therapeutic effect on the treated subject.

The interrelationship of dosages for animals and humans (based on milligrams per meter squared of body surface) is described in Freireich et al., (1966) *Cancer Chemother Rep* 50: 219. Body surface area may be approximately determined from height and weight of the patient. See, e.g., Scientific Tables, Geigy Pharmaceuticals, Ardley, N.Y., 1970, 537. An effective amount of the piperazinedione compounds can range from about 0.1 mg/Kg to about 50 mg/Kg. Effective doses will also vary, as recognized by those skilled in the art, depending on the types of tumors treated, route of administration, excipient usage, and the possibility of co-usage with other therapeutic treatments such as use of other anti-tumor agents or radiation therapy.

To practice the method of the present invention, a piperazinedione compound-containing composition can be administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional and intracranial injection or infusion techniques.

A sterile injectable composition, for example, a sterile injectable aqueous or oleaginous suspension, can be formulated according to techniques known in the art using suitable dispersing or wetting agents (such as, for example, Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

A composition for oral administration can be any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added. A nasal aerosol or inhalation composition can be prepared according to techniques well-known in the art of pharmaceutical formulation and can be prepared as solutions in saline, employing benzyl alcohol or other suitable preservatives, absorption promoters to enhance bioavailability, fluorocarbons, and/or other solubilizing or dispersing agents known in the art. A piperazinedione compound-containing composition can also be administered in the form of suppositories for rectal administration.

The carrier in the pharmaceutical composition must be "acceptable" in the sense of being compatible with the active ingredient of the formulation (and preferably, capable of stabilizing it) and not deleterious to the subject to be treated. For example, solubilizing agents such as cyclodextrins, which form specific, more soluble complexes with the piperazinedione compounds, or one or more solubilizing agents, can be utilized as pharmaceutical excipients for delivery of the piperazinedione compounds. Examples of other carriers include colloidal silicon dioxide, magnesium stearate, cellulose, sodium lauryl sulfate, and D&C Yellow #10.

The piperazinedione compounds can be preliminarily screened for their efficacy in treating cancer by one or more of the following in vitro assays.

One assay is based on the NCI screening system, which consists of approximately 60 cell lines of major human tumors. See Monks, et al. (1991) *JNCI, J Natl. Cancer Inst.* 83: 757–766; Alley, et al. (1988) *Cancer Res.* 48: 589–601; Shoemaker, et al. (1988) *Proc. Clin. Biol. Res.* 276: 265–286; and Stinson, et al. (1989) *Proc. Am. Assoc. Cancer Res.* 30: 613. Briefly, a cell suspension that is diluted according to the particular cell type and the expected target cell density (5,000–40,000 cells per well based on cell growth characteristics) is added (100 $\mu$L) into a 96-well microtiter plate. A pre-incubation is preformed at 37° C. for 24 hr. Dilutions at twice of an intended test concentration are added at time zero in 100 $\mu$L aliquots to each well of the microtiter plate. Usually, a test compound is evaluated at five 10-fold dilutions. In a routine testing, the highest concentration of the test compound is $10^{-4}$ M. Incubations are performed for 48 hr in 5% $CO_2$ atmosphere and 100% humidity. The cells are assayed by using the sulforhodamine B assay described by Rubinstein, et al. (1990, *JNCI, J Natl. Cancer Inst.* 82: 1113–1118) and Skehan, et al. (1990, *JNCI, J. Natl. Cancer Inst.* 82: 1107–1112). A plate reader is used to read the optical densities and a microcomputer processes the optical densities into the special concentration parameters. The NCI has renamed an $IC_{50}$ value, the concentration that causes 50% growth inhibition, a $GI_{50}$ value to emphasize the correction for the cell counted at time zero; thus, the $GI_{50}$ measures the growth inhibitory power of the test compound. See Boyd, et al. (1992) In *Cytotoxic Anticancer Drugs: Models and Concepts for Drug Discovery and Development;* Vleriote, F. A.; Corbett, T. H.; Baker, L. H. (Eds.); Kluwer Academic: Hingham, Mass., pp 11–34.

In another assay, a piperazinedione compound is tested for its cytotoxicity on PC-3 cells (a prostate cancer cell line). More specifically, cells are incubated with a test compound in a serum-free medium for 24 hr. The cytotoxic effect can be determined using the 3-(4,5-dimethylthiazol-2-yl)-2,5-diphenyltetrazolium bromide (MTT) assay method described in Boyd (In *Principle of Practice of Oncology* Devita, J. T., Hellman, S., and Rosenberg, S. A. (Eds.) Vol. 3, PPO Update, No. 10, 1989).

Another in vitro assay can be used to evaluate the efficiency of a piperazinedione compound in arresting the cell cycle progression. More specifically, a test piperazinedione compound is added to PC-3 cells in a concentration-dependent manner using propidium iodide-stained flow cytometric assessment. The cell population of sub-$G_0/G_1$, $G_0/G_1$, S, and $G_2/M$ phase is then determined. In addition, the effect of a piperazinedione compound on the Ras activity can be examined to determine its regulation of Ras protein-dependent signal transduction pathway.

The anti-tumor activity of a piperazinedione compound can be further assessed by an in vivo animal model. Using SCID mice as the model, PC-3 cells are subcutaneously injected into the mice to develop a prostate tumor. The anti-tumor activity of a piperazinedione compound is determined after treatment. Additionally, the anti-tumor activity of a piperazinedione compound can also be evaluated using in vivo anti-angiogenesis testing. For example, nude mice can be used to test the effect of a piperazinedione compound on bFGF-induced angiogenesis. A matrigel with bFGF or vscular endothelial growth factor (VEGF) is subcutaneously injected into a mouse with concurrent intraperitoneal administration of a piperazinedione compound. After several days of incubation, the matrigel is cut down for examination of angiogenesis.

Without further elaboration, it is believed that the above description has adequately enabled the present invention. The following specific embodiments are, therefore, to be construed as merely illustrative, and not limitative of the remainder of the disclosure in any way whatsoever. All of the publications cited herein are hereby incorporated by reference in their entirety.

EXAMPLE 1

Synthesis of 3-[(5-benzyloxypyridin-2-yl) methylidene]-6-phenylmethylidene piperazine-2,5-dione (Compound 1)

1,4-Diacetyl-piperazine-2,5-dione (8.6 g) was added to a solution of 5-benzyoxypyridin-2-yl-formaldehyde (4.0 g) in 5.6 mL of triethylamine and 40 mL of dimethylformamide. The mixture was stirred at room temperature for 16 hr and then cooled at ice bath to produce a yellow precipitate. The precipitate was then collected and washed with ethyl acetate to give 5.4 g (77%) of 1-acetyl-3-[(5-benzyoxypyridin-2-yl) methylidene]piperazine-2,5-dione (Compound A).

mp: 189–191° C.

$^1$HNMR (400 MHz, DMSO): $\delta$2.52 (s, 3H), $\delta$4.54 (s, 3H), $\delta$4.33 (s, 2H), $\delta$5.25 (s, 2H), $\delta$6.85 (s, 1H), $\delta$7.384~$\delta$7.488 (m, 5H), aromatic), $\delta$7.499 (d, J=8.8, 1H), $\delta$7.689 (d, J=8.8, 1H), $\delta$8.533 (s, 1H), and $\delta$12.147 (s, 1H).

Compound A (3.51 g) was added to a 40 mL of dimethylformamide solution containing equal molar of benzaldehyde and 4 equivalents of triethylamine. The solution was refluxed at 60° C. for 16 hr and cooled at ice bath to produce a yellow precipitate. The precipitate was then collected and washed with ethyl acetate to give 3.3 g (83%) of the desired product 3-[(5-benzyoxypyridin-2-yl)methylidene]-6-phenylmethylidenepiperazine-2,5-dione (Compound 1) as a mixture of isomers. The mixture was predominately the ZZ and EZ isomers.

mp: 223–225° C.

$^1$HNMR (400 MHz, DMSO): $\delta$5.243 (s, 2H), $\delta$6.695 (s, 1H), $\delta$6.812 (s, 1H), $\delta$7.346~$\delta$7.634 (m, 12H, aromatic), $\delta$8.528 (s, 1H), $\delta$10.245 (s, 1H), and $\delta$12.289 (s, 1H).

EXAMPLE 2

Synthesis of 3-[(5-benzyloxypyridin-2-yl) methylidene]-6-p-hydroxyphenyl methylidenepiperazine-2,5-dione (Compound 2)

Compound A (3.51 g), obtained from Example 1, was added to a 40 mL of dimethylformamide solution containing 1.5 g of 4-hydroxybenzaldehyde and 4 equivalents of triethylamine. The solution was refluxed at 130° C. for 16 hr and cooled at ice bath to produce a yellow precipitate. The precipitate was then collected and washed with ethyl acetate to give 3.3 g (83%) of the desired 3-[(5-benzyoxypyridin-2-yl) methylidene]-6-p-hydroxyphenylmethylidenepiperazine-2,5-dione (Compound 2).

mp: 260–263° C.

$^1$HNMR (400 MHz, DMSO): $\delta$5.244 (s, 2H), $\delta$6.669 (s, 1H), $\delta$6.753 (s, 1H), $\delta$6.798 (s, 1H), 1H, aromatic), $\delta$6.819 (s, 1H, aromatic), $\delta$7.347~$\delta$7.647 (m, 9H, aromatic), $\delta$9.821 (s, 1H), $\delta$10.064 (s, 1H), and $\delta$12.216 (s, 1H).

EXAMPLE 3

Synthesis of 3-[(5-benzyloxypyridin-2-yl) methylidene]-6-p-methoxyphenyl methylidenepiperazine-2,5-dione (Compound 3)

Compound A (3.51 g), obtained from Example 1, was added to a 40 mL of dimethylformamide solution containing 1.4 g of 4-methoxybenzaldehyde and 4 equivalents of triethylamine. The solution was reluxed at 130° C. for 16 hr and cooled at ice bath to produce a yellow precipitate. The precipitate was then collected and washed with ethyl acetate to give 3.3 g (83%) of the desired 3-[(5-benzyoxypyridin-2-yl) methylidene]-6-methoxyphenylmethylidenepiperazine-2,5-dione (Compound 3).

mp: 238–240° C.

$^1$HNMR (400 MHz, DMSO): $\delta$5.244 (s, 2H), $\delta$6.669 (s, 1H), $\delta$6.753 (s, 1H), $\delta$6.798 (s, 1H, aromatic), $\delta$6.819 (s, 1H, aromatic), $\delta$7.347~$\delta$7.647 (m, 9H, aromatic), $\delta$9.821 (s, 1H), $\delta$10.064 (s, 1H), and $\delta$12.216 (s, 1H).

EXAMPLE 4

Synthesis of 3-[(5-benzyloxypyridin-2-yl) methylidene]-6-p-fluorophenyl (methylidenepiperazine-2,5-dione (Compound 4)

Compound A (3.51 g), obtained from Example 1, was added to a 40 mL of dimethylformamide solution containing 1.3 g of 4-fluoro benzaldehyde and 4 equivalents of triethylamine. The solution was refluxed at 130° C. for 16 hr and cooled at ice bath to produce a yellow precipitate. The precipitate was then collected and washed with ethyl acetate to give 3.12 g (75%) of the desired 3-[(5-benzyoxypyridin-2-yl)methylidene]-6-p-fluorophenylmethylidenepiperazine-2,5-dione (Compound 4).

mp: 242–244° C.

$^1$HNMR (400 MHz, DMSO): $\delta$5.237 (s, 2H), $\delta$6.688 (s, 1H), $\delta$6.794 (s, 1H), $\delta$7.209~$\delta$7.624 (m, 11H, aromatic), $\delta$8.520 (s, 1H), $\delta$10.348 (s, 1H), and $\delta$12.279 (s, 1H).

EXAMPLE 5

Synthesis of 3-[(5-benzyloxypyridin-2-yl) methylidene]-6-p-chlorophenyl methylidenepiperazine-2,5-dione (Compound 5)

Compound A (3.51 g), obtained from Example 1, was added to a 40 mL of dimethylformamide solution containing 1.3 g of 4-chlorobenzaldehyde and 4 equivalents of triethylamine. The solution was refluxed at 130° C. for 16 hr and cooled at ice bath to produce a yellow precipitate. Then the precipitate was collected and washed with ethyl acetate to give 3.45 g (80%) of the desired 3-[(5-benzyoxypyridin-2-yl)methylidene]-6-p-chlorophenylmethylidenepiperazine-2,5-dione (Compound 5).

mp: 250–251° C.

EXAMPLE 6

Synthesis of 3-[(5-benzyloxypyridin-2-yl) methylidene]-6-p-benzyoxyphenylmethylidene piperazine-2,5-dione (Compound 6)

Compound A (3.51 g), obtained from Example 1, was added to a 40 mL of dimethylformamide solution containing 1.45 g of 4-benzyoxybenzaldehyde and 4 equivalents of triethylamine. The solution was refluxed at 130° C. for 16 hr and cooled at ice bath to produce a yellow precipitate. The precipitate was then collected, washed with ethyl acetate, and recrystallized from dimethylformamide to give 3.45 g (80%) of the desired 3-[(5-benzyoxypyridin-2-yl) methylidene]-6-p-benzyoxyphenylmethylidene piperazine-2,5-dione (Compound 6).

mp: 253–255° C.

$^1$HNMR (400 MHz, DMSO): δ5.142 (s, 2H), δ5.235 (s, 2H), δ6.672 (s, 1H), δ6.777 (s, 1H), δ7.041~δ7.639 (m, 16H, aromatic), δ8.520 (s, 1H), δ10.180 (s, 1H), and δ12.235 (s, 1H).

EXAMPLE 7

Synthesis of 3-[(5-benzyloxypyridin-2-yl) methylidene]-6-[(furan-2-yl) methylidene] piperazine-2,5-dione (Compound 7)

Compound A (2.8 g), obtained from Example 1, was added to a 40 mL of dimethylformamide solution containing 2 mL of furfural and 4 equivalents of triethylamine. The solution was refluxed at 60° C. for 48 hr and cooled at ice bath to produce a yellow precipitate. The precipitate was then collected, washed with ethyl acetate, and recrystallized from dimethylformamide to give 2.5 g (80%) of the desired 3-[(5-benzyoxypyridin-2-yl)methylidene]-6-[(furan-2-yl) methylidene]piperazine-2,5-dione (Compound 7).

mp: 256–257° C.

$^1$HNMR (400 MHz, DMSO): δ5.245 (s, 2H), δ6.656 (d, J=1.6, 1H), δ6.664 (d, J=1.6, 1H), δ6.685 (s, 1H), δ6.720 (s, 1H), δ7.349~δ7.942 (m, 8H, aromatic), δ8.527 (s, 1H), δ9.515 (s, 1H), and δ12.312 (s, 1H).

EXAMPLE 8

Synthesis of 3-[(5-benzyoxypyridin-2-yl) methylidene]-6-[(thien-2-yl) methylidene] piperazine-2,5-dione (Compound 8)

Compound A (2.8 g), obtained from Example 1, was added to a 40 mL of dimethylformamide solution containing 2 mL of thiophene-2-carbaldehyde and 4 equivalents of triethylamine. The solution was refluxed at 60° C. for 2 days and cooled at ice bath to produce a yellow precipitate. The precipitate was then collected, a washed with ethyl acetate, and recrystallized from dimethylformamide to give 1.9 g (59%) of the desired 3-[(5-benzyoxypyridin-2-yl) methylidene]-6-[(thiophene-2-yl)methylidene] piperazine-2,5-dione (Compound 8).

mp: 215–217° C.

$^1$HNMR (400 MHz, DMSO): δ5.245 (s, 2H), δ6.716 (s, 1H), δ6.974 (s, 1H), δ7.186 (s, 1H), δ7.384~δ7.746 (m, 9H, aromatic), δ8.525 (s, 1H), δ9.753 (s, 1H), and δ12.288 (s, 1H).

EXAMPLE 9

Synthesis of 3-[(5-benzyloxypyridin-2-yl) methylidene]-6-[(2-pyridinyl) methylidene] piperazine-2,5-dione (Compound 9)

Compound A (2.8 g), obtained from Example 1, was added to a 40 mL of dimethylformamide solution containing 2 mL of pyridine-2-carbaldehyde and 4 equivalents of triethylamine. The solution was refluxed at 60° C. for 2 days and cooled at ice bath to produce a yellow precipitate. The precipitate was then collected, a washed with ethyl acetate, and recrystallized from dimethylformamide to give 2.7 g (85%) of the desired 3-[(5-benzyloxypyridin-2-yl) methylidene]-6-[(2-pyridinyl)methylidene] piperazine-2,5-dione (Compound 9).

mp: 248–250° C.

$^1$HNMR (400 MHz, DMSO): δ5.246 (s, 2H), δ6.709 (s, 1H), δ6.788 (s, 1H), δ7.349~δ7.661 (m, 8H, aromatic), δ7.923 (d, J=8, 1H, aromatic), δ8.473 (d, J=3.6, 1H), δ8.533 (d, J=2.8, 1H), δ8.680 (d, J=2, 1H), δ10.667 (s, 1H), and δ12.324 (s, 1H).

EXAMPLE 10

Synthesis of 3,6-di[[(5-phenylmethoxypyridin-2-yl) methylidene]piperazine-2,5-dione (Compound 10)

Compound A (0.31 g), obtained from Example 1, was added to a 40 mL of dimethylformamide solution containing equal molar of 5-benzyoxypyridin-2-yl-formaldehyde and 4 equivalents of triethylamine. The solution was refluxed at 130° C. overnight and cooled at ice bath to produce a yellow precipitate. The precipitate was then collected and washed with ethyl acetate to give 0.36 g (80%) of the desired 3,6-di[[(5-phenylmethoxypyridin-2-yl)methylidene] piperazine-2,5-dione (Compound 10).

mp: 283–28° C.

$^1$HNMR (400 MHz, DMSO): δ5.145 (s, 4H), δ6.780 (s, 2H), δ7.240~δ7.394 (m, 14H, aromatic), δ8.381 (s, 2H), δ10.145 (s, 1H), and δ12.58 (s, 1H).

EXAMPLE 11

Synthesis of 3-[(5-phenylmethoxypyridin-2-yl) methylidene]-6-(2-oxo-3-indolylidenepiperazine-2, 5-dione (Compound 11)

Compound A (2.8 g), obtained from Example 1, was added to a 40 mL of dimethylformamide solution containing 1.5 g of isatine and 4 equivalent of triethylamine. The solution was refluxed at 130° C. for 2 hr and cooled at ice bath to produce a yellow precipitate. The precipitate was then collected and washed with ethyl acetate to give 3.04 g (87%) of the desired 3-[(5-phenylmethoxypyridin-2-yl) methylidene]-6-(2-oxo-3-indolylidenepiperazine-2,5-dione (Compound 11).

mp: >300° C.

EXAMPLE 12

Synthesis of 1-acetyl-3-[(5-benzyloxypyridin-2-yl) methyl]piperazine-2,5-dione (Compound 12)

A suspension of 3.51 g of 1,4-diacetyl-piperazine-2,5-dione and excess of zinc powder in a mixture of 100 mL of acetic acid and 10 mL of water was stirred and refluxed for 5–10 minutes and cooled. The mixture was filtered. The solid thus obtained was collected and washed with water to give 2.0 g of the desired 1-acetyl-3-[(5-benzyoxypyridin-2-yl)methyl]piperazine-2,5-dione (Compound 12).

mp: 215–216° C.

EXAMPLE 13

Synthesis of 3,6-di[[(5-benzyloxypyridin-2-yl) methyl]piperazine-2,5-dione (Compound 13)

A suspension of 3,6-di[(5-benzyoxypyridin-2-yl) methylidene]piperazine-2,5-dione (0.2 g) and excess of zinc powder in a mixture of 10 mL of acetic acid and 10 mL of water was stirred and refluxed for 5–10 minutes and filtered while hot. Water was added to dissolve zinc acetate. The filtrate was concentrated and filtered. The solid thus obtained was collected and washed with water to give 80 mg (40%) of the desired 3,6-di[(5-benzyoxypyridin-2-yl)methyl] piperazine-2,5-dione (Compound 13).

mp: 228–231° C.

EXAMPLE 14

Synthesis of 3-[(5-acetoxypyridin-2-yl) methylidene]-6-(benzylmethylidene) piperazine-2,5-dione (Compound 14)

3-[(5-benzyloxypyridin-2-yl)methylidene]-6-(benzylmethylidene)piperazine-2,5-dione (Compound 1, 0.5 g, 1.26 mmol) and NaOH (0.5 g, 12.5 mmol) were dissolved in 100 mL of methanol. The mixture was hydrogenated with 0.5 g palladium/charcoal under 1 atmospheric pressure. After completing the reaction as monitored by TLC, the catalyst was removed by filtration and the filtrate was evaporated in vacuo to produce a reside. The residue was added with 50 mL water and the obtained aqueous solution was adjusted to pH=7. A precipitated was formed and collected to obtain a 0.27 g product of 3-[(5-hydroxypyridin-2-yl)methylidene]-6-(benzylmethylidene)piperazine-2,5-dione (Compound B) (70% yield).

$^1$HNMR (400 MHz, CDCl$_3$): $\delta$6.758 (s, 1H), $\delta$7.087 (s, 1H), $\delta$7.290~$\delta$7.580 (m, 7H, aromatic), $\delta$8.328 (s, 1H), and $\delta$12.289 (s, 1H).

A solution of compound B (0.05 g, 0.16 mmole) in acetic anhydride (50 mL) was refluxed at 150° C. for 24 hrs. The unreacted acetic anhydride and produced acetic acid were removed in vacuo to obtain a residue. The residue was chromatographed using silica gel column with a developing solvent (CH$_2$Cl$_2$:MeOH=9:1) to give 0.051 g (90%) of Compound 14 as a mixture of isomers. The mixture was predominately the ZZ isomer.

$^1$HNMR (400 MHz, CDCl$_3$): $\delta$2.377 (s, 3H), $\delta$6.786 (s, 1H), $\delta$7.107 (s, 1H), $\delta$7.368~$\delta$8.496 (m, 7H, aromatic), $\delta$8.224 (s, 1H), and $\delta$12.498 (s, 1H).

EXAMPLE 15

Synthesis of 3-[(5-benzoyloxypyridin-2-yl) methylidene]-6-(benzylmethylidene)piperazine-2,5-dione (Compound 15)

A reaction mixture containing compound B (0.05 g, 0.16 mmole; obtained from Example 14), benzoyl chloride (15 ml, 0.16 mmole) and 50 mL of chloroform was heated to 150° C. for 2 hr. Chloroform was removed in vacuo to produce a residue. The residue was chromatographed using silica gel column with a developing solvent (CH$_2$Cl$_2$) to give 0.007 g (10%) of Compound 15.

$^1$HNMR (400 MHz, CDCl$_3$): $\delta$6.786 (s, 1H), $\delta$7.107 (s, 1H), $\delta$7.368~$\delta$8.496 (m, 13H, aromatic), and $\delta$8.223 (s, 1H).

EXAMPLE 16

Synthesis of 3-[(5-(4-toluenesulfonyl)pyridin-2-yl) methylidene]-6-(benzylmethylidene)piperazine-2,5-dione (Compound 16)

A reaction mixture of compound B (0.05 g, 0.16 mmole; obtained from Example 14), toluenesulfonyl chloride (0.03 g, 0.16 mmole), and 50 mL of toluene was heated to 150° C.
for 2 hr. Toluene was removed in vacuo to produce a residue. The residue was chromatographied using silica gel column with a developing solvent (CH$_2$Cl$_2$) to give 0.007 g (10%) of Compound 16.

$^1$HNMR (400 MHz, CDCl$_3$): $\delta$2.503 (s, 3H), $\delta$6.751 (s, 1H), $\delta$7.102 (s, 1H), $\delta$7.343~$\delta$8.159 (m, 12H, aromatic), $\delta$8.223 (s, 1H), and $\delta$12.315 (s, 1H).

EXAMPLE 17

Synthesis of 3-[(5-(4-chlorophenylcarbamic)pyridin-2-yl)methylidene]-6-(benzylmethylidene)piperazine-2,5-dione (Compound 17)

A reaction mixture of compound B (0.05 g, 0.16 mmole; obtained from Example 14), 4-chlorophenylisocyanate (0.024 g, 0.16 mmole), and 50 mL of chloroform was heated to 100° C. for 24 hr. Chloroform was removed in produce a residue. The residue was chromatographied using silica gel column with a developing solvent (CH$_2$Cl$_2$) to give 0.01 g (15%) of Compound 17.

EXAMPLE 18

Screening for Anti-Tumor Activities (NCI Cell Lines)

The cytotoxic activities of a number of piperazinedione compounds were measured against a panel of 60 different NCI human tumor cell lines.

All test compounds were found to be active. The least potent compound exhibited GI$_{50}$ values <10$^{-4}$ M for 4 cell lines. The most potent compound exhibited GI$_{50}$ values <10$^{-4}$ M for all 60 cell lines, with GI$_{50}$ values <10$^{-8}$ M for 9 cell lines.

EXAMPLE 19

Screening for Anti-Tumor Activities (A Prostate Cell Line)

The cytotoxic activities of a number of piperazinedione compounds and taxol (a well-known anti-tumor agent) were tested on PC-3 cells. Cells were incubated in the presence of each compound in a serum-free medium for 24 hr. The cytotoxic activities were determined by the MTT assay. All test compounds are active. Unexpectively, the most potent piperazinedione compound has an EC$_{50}$ value around 0.3 microM, >30 times more potent than taxol.

EXAMPLE 20

In vitro Assay (Inhibition of G$_2$/M Progression of the Cell Cycle)

PC-3 cells were incubated in the presence of a piperazinedione compound in a serum-free medium and harvested, fixed, and stained with propidium iodide at the 6$^{th}$, 12$^{th}$, 18$^{th}$, and 24$^{th}$ hr, respectively. The stage of cell cycles was determined based on flow cytometric measurements. The test compound induced an arrest of the cell cycle as entranced by a large number of cells at G$_2$/M phase. In addition, a piperazinedione compound had a marked effect on the regulation of Ras activity

EXAMPLE 21

In Vitro Assay (Disturbance of Tubulin/ Microtubulin Assembly)

Tubulin/microtubulin was incubated in the presence of a piperazinedione compound at different concentrations in a solution (0.1 M MES, 1 mM EGTA, 0.5 mM $MgCl_2$, 0.1 mM EDTA, and 2.5 M glycerol) at 37° C. Then, GTP was added to induce polymerization of tubulin/microtubulin. Optical density (OD) was measured at 350 nm at various time points to determine the degree of the polymerization. The test compound inhibited the polymerization at $10^{-6}$–$10^{-5}$ M.

EXAMPLE 22
In vivo Assay (Inhibition of Tumor Enlargement)

SCID mice, subcutaneously injected into PC-3 cells, developed a tumor more than 800 $mm^3$ in volume. A piperazinedione compound significantly diminished the tumor volume after a 14–28 days treatment.

EXAMPLE 23
In vivo Assay (Regulation of Angiogenesis Activity)

After subcutaneous incubation of a bFGF or VEGF-containing matrigel plug (0.5 mL/20 g mouse) for 6 days, a significant angiogenic effect was detected in the plug. Intra-peritoneal injection of a piperazinedione compound almost completely diminished the angiogenic effect.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. For example, compounds structurally analogous the piperazinedione compounds of this invention also can be made, screened for their anti-tumor activities, and used to practice this invention. Thus, other embodiments are also within the claims.

What is claimed is:

1. A compound having the following formula:

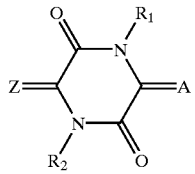

wherein

A is $C(R^a R^b)$;

Z is $R_3O$—(Ar)—B, in which B is $C(R^c)$; Ar is pyridyl linked to B at position 2; and $R_3$ is H, alkyl substituted with aryl, or aryl; in which aryl is unsubstituted or substituted with one or more substitutents selected from the group consisting of halogen, hydroxyl, amino, alkylamino, arylamino, dialkylamino, diarylamino, cyano, nitro, mercapto, carbamido, carbamoyl, carboxyl, thioureido, thiocyanato, sulfonamido, $C_-$–$C_6$ alkyl, $C_2$–$C_6$ alkenyl, $C_1$–$C_6$ alkoxy, and aryl;

each of $R_1$ and $R_2$, independently, is H, or $C(O)R^d$; and one of $R^a$ and $R^b$ is thienyl, furyl, pyridinyl, indolyl, 2-oxo-indolyl, aryl, alkyl, or alkyl substituted with aryl, and each of the other of $R^a$ and $R^b$, and $R^c$, and $R^d$, independently, is H, alkyl, or aryl; in which alkyl and aryl are unsubstituted or substituted with one or more substitutents selected from the group consisting of halogen, hydroxyl, amino, alkylamino, arylamino, dialkylamino, diarylamino, cyano, nitro, mercapto, carbamido, carbamoyl, carboxyl, thioureido, thiocyanato, sulfonamido, $C_1$–$C_6$ alkyl, $C_2$–$C_6$ alkenyl, $C_1$–$C_6$ alkoxy, and aryl.

2. The compound of claim 1, wherein $R^c$ is H.

3. The compound of claim 2, wherein $R_3O$ is linked to position 5 of pyridyl.

4. The compound of claim 3, wherein $R_3O$ is arylalkoxy.

5. The compound of claim 4, wherein both $R_1$ and $R_2$ are H.

6. The compound of claim 5, wherein one of $R^a$ and $R^b$ is aryl or thienyl, furyl, pyridinyl, indolyl or 2-oxo-indolyl, and the other of $R^a$ and $R^b$ is H.

7. The compound of claim 6, wherein $R_3O$ is benzyloxy.

8. The compound of claim 1, wherein $R_3O$ is arylalkoxy.

9. The compound of claim 1, wherein both $R_1$ and $R_2$ are H.

10. The compound of claim 9, wherein $R^c$ is H.

11. The compound of claim 1, wherein one of $R^a$ and $R^b$ is aryl or thienyl, furyl, pyridinyl, indolyl or 2-oxo-indolyl, and the other of $R^a$ and $R^b$ is H.

12. The compound of claim 11, wherein $R^c$ is H.

13. The compound of claim 12, wherein $R_3O$ is arylalkoxy linked to position 5 of pyridyl.

14. The compound of claim 1, wherein the compound is

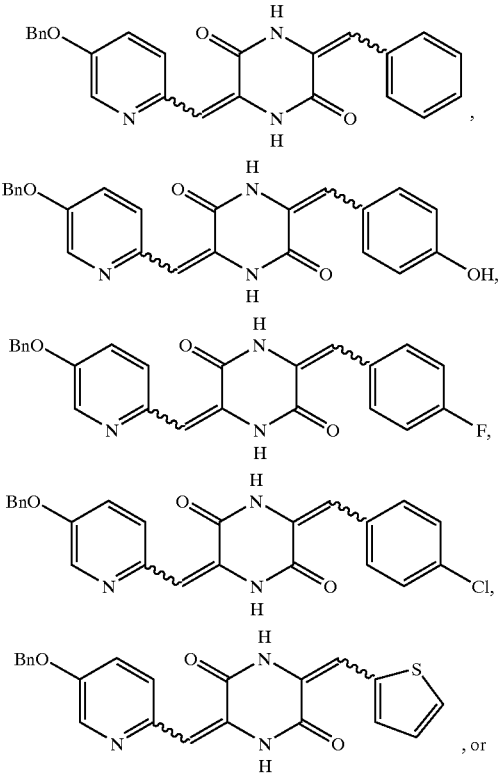

-continued

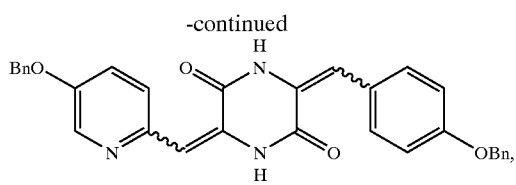

wherein Bn is benzyl.

15. The compound of claim 14, wherein the compound is

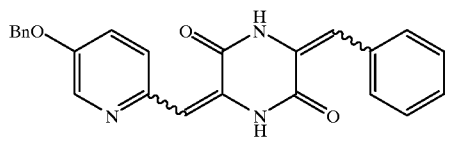

16. The compound of claim 14, wherein the compound is

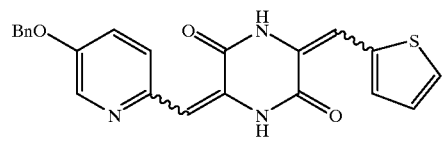

17. A method for treating tumor, comprising administering to a subject in need thereof an effective amount of the compound having the formula:

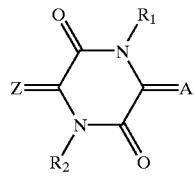

wherein

A is $C(R^a R^b)$;

Z is $R_3O—(Ar)—B$, in which B is $C(R^c)$; Ar is pyridyl linked to B at position 2; and $R_3$ is H, alkyl substituted with aryl, or aryl; in which aryl is unsubstituted or substituted with one or more substitutents selected from the group consisting of halogen, hydroxyl, amino, alkylamino, arylamino, dialkylamino, diarylamino, cyano, nitro, mercapto, carbamido, carbamoyl, carboxyl, thioureido, thiocyanato, sulfonamido, $C_1$~$C_6$ alkyl, $C_2$~$C_6$ alkenyl, $C_1$~$C_6$ alkoxy, and aryl;

each of $R_1$ and $R_2$, independently, is H, or $C(O)R^d$; and one of $R^a$ and $R^b$ is thienyl, furyl, pyridinyl, indolyl, 2-oxo-indolyl, aryl, alkyl, or alkyl substituted with aryl, and each of the other of $R^a$ and $R^b$, and $R^c$, and $R^d$, independently, is H, alkyl, or aryl; in which alkyl and aryl are unsubstituted or substituted with one or more substitutents selected from the group consisting of halogen, hydroxyl, amino, alkylamino, arylamino, dialkylamino, diarylamino, cyano, nitro, mercapto, carbamido, carbamoyl, carboxyl, thioureido, thiocyanato, sulfonamido, $C_1$~-$C_6$ alkyl, $C_2$~$C_6$ alkenyl, $C_1$~-$C_6$ alkoxy, and aryl.

18. The method of claim 17, wherein the pyridyl is substituted with arylalkoxy at position 5.

19. The method of claim 17, wherein both $R_1$ and $R_2$ are H.

20. The method of claim 17, wherein one of $R^a$ and $R^b$ is aryl or thienyl, furyl, pyridinyl, indolyl or 2-oxo-indolyl, and the other of $R^a$ and $R^b$ is H.

21. The method of claim 17, wherein the compound is

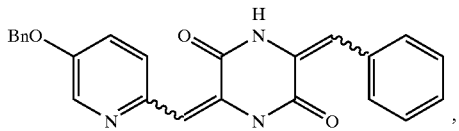,

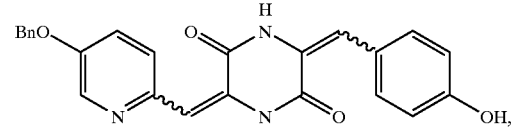,

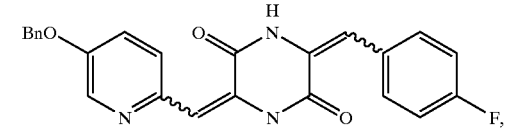,

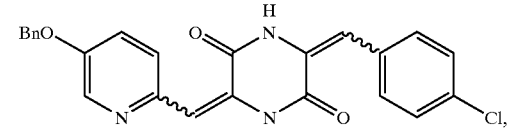,

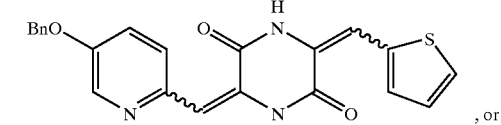, or

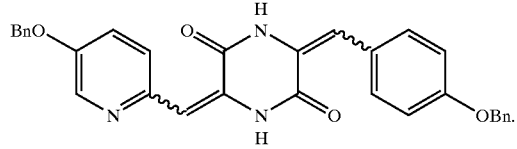.

22. The method of claim 21, wherein the compound is

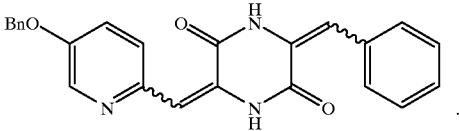.

23. The method of claim 21, wherein the compound is

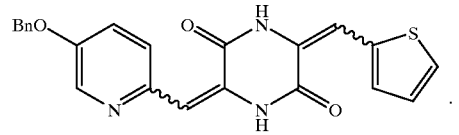.

* * * * *